United States Patent [19]

Silberstone et al.

[11] Patent Number: 5,052,391

[45] Date of Patent: Oct. 1, 1991

[54] HIGH FREQUENCY HIGH INTENSITY TRANSCUTANEOUS ELECTRICAL NERVE STIMULATOR AND METHOD OF TREATMENT

[75] Inventors: Leon M. Silberstone, LaJolla, Calif.; Michael E. Halleck, Longmont, Colo.

[73] Assignee: R.F.P., Inc., Aurora, Colo.

[21] Appl. No.: 601,150

[22] Filed: Oct. 22, 1990

[51] Int. Cl.⁵ ............................................. A61N 1/34
[52] U.S. Cl. .................................................. 128/422
[58] Field of Search .................. 128/419 R, 421, 422; 600/27; 606/32, 40, 52

[56] References Cited

U.S. PATENT DOCUMENTS

| | | | |
|---|---|---|---|
| 2,700,975 | 2/1985 | Hopfinger et al. | 606/36 |
| 2,771,554 | 11/1956 | Gratzl | 128/421 |
| 3,810,457 | 5/1974 | Bottcher et al. | 128/421 |
| 3,909,502 | 9/1975 | Liss et al. | 128/422 |
| 4,055,190 | 10/1977 | Tany | 128/422 |
| 4,093,975 | 6/1978 | Roberts | 128/419 R |
| 4,237,896 | 12/1980 | Lines | 128/419 R |
| 4,305,402 | 12/1981 | Katims | 128/421 |
| 4,324,253 | 4/1982 | Gregne et al. | 128/421 |
| 4,566,454 | 1/1986 | Mehl et al. | 606/36 |

Primary Examiner—William E. Kamm
Attorney, Agent, or Firm—Holland & Hart

[57] ABSTRACT

A transcutaneous electrical nerve stimulation (TENS) device provides significantly improved patient results by supplying high frequency electrical pulses at frequencies in a range of 2.5 to 60 kilohertz. The frequency and intensity of the pulses can be adjusted, to treat the patient at the optimal frequency and amplitude in order to treat chronic or acute pain or to block the pain caused by a traumatic or medical procedure. Starting at a mid-level of intensity where no stimulation occurs, the frequency is adjusted downwardly until there is some nerse sensation. At this point, the procedure may be performed while the frequency is adjusted downwardly as needed to maintain nerve sansation. The wave form characteristic of the pulses is an AC wave form with a square wave portion with rapid rise time and slower fall time followed by a pulse portion of the opposite polarity compared to the square wave portion.

20 Claims, 4 Drawing Sheets

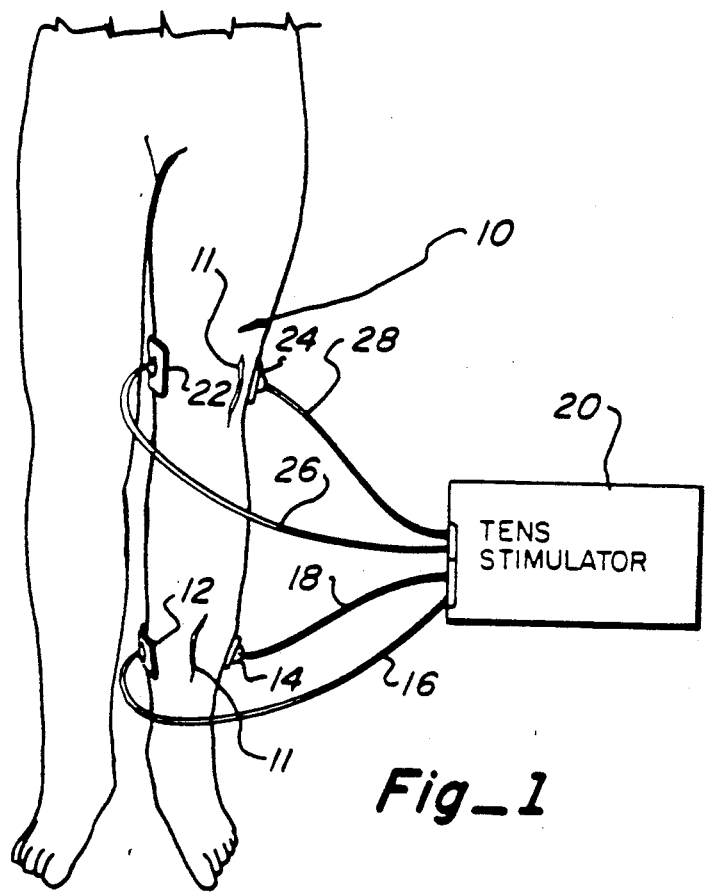
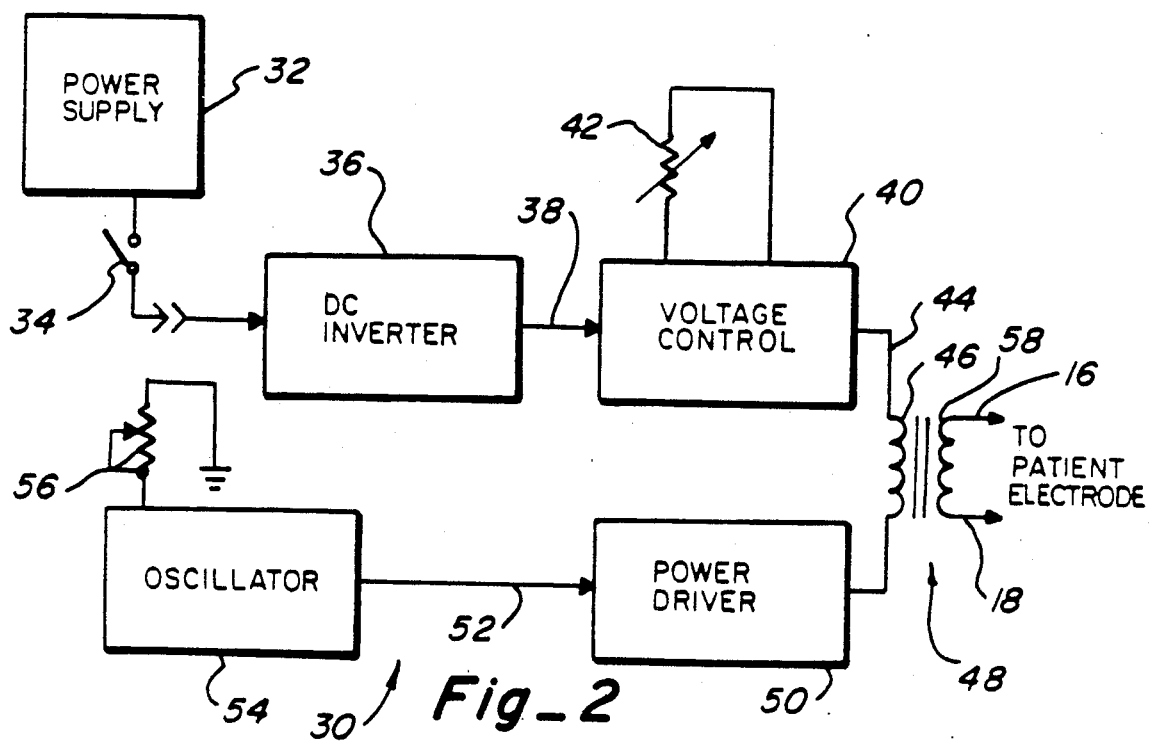

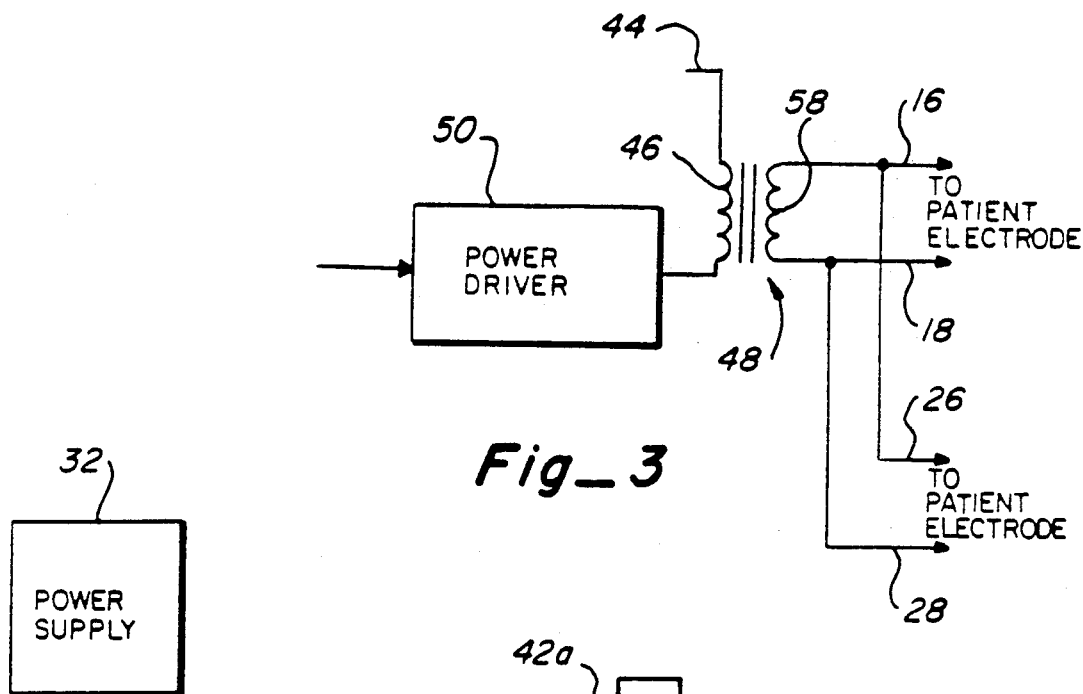
Fig_3
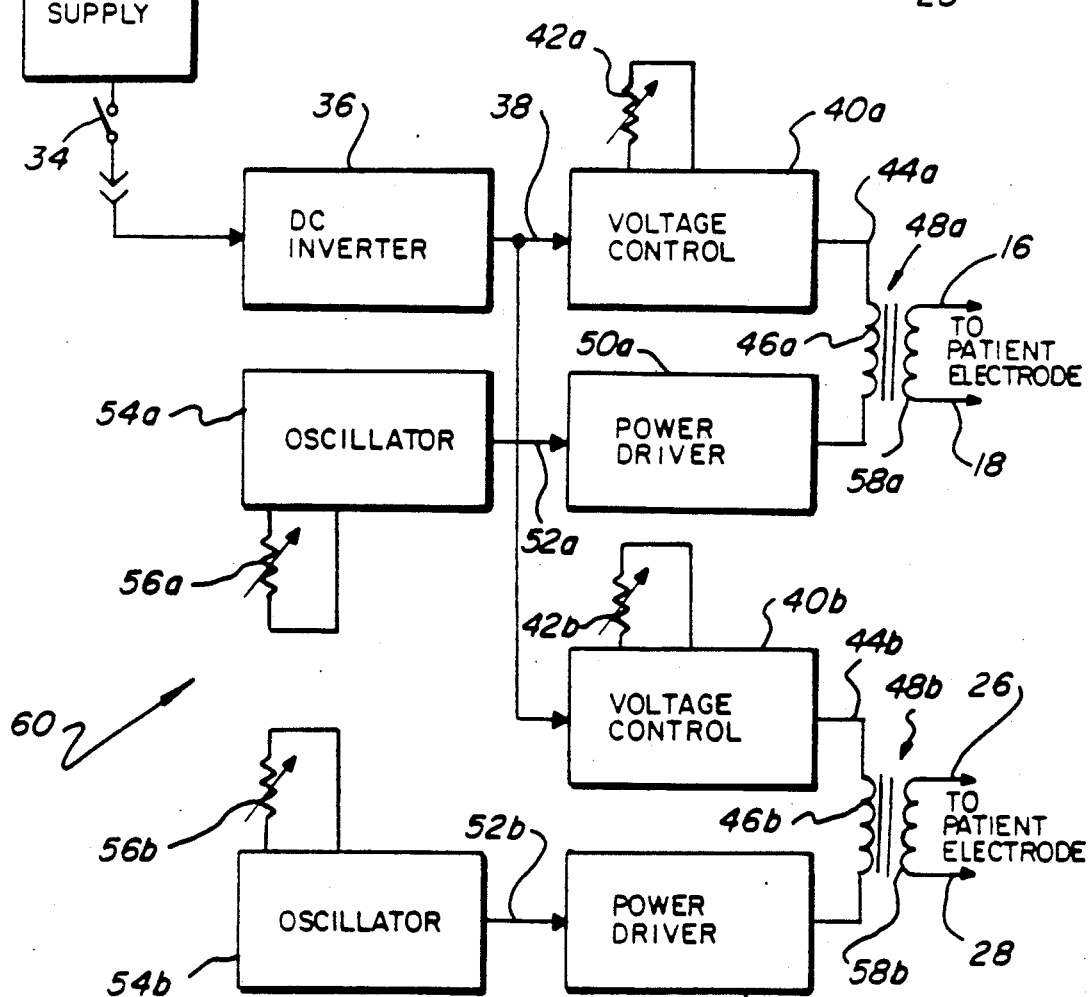
Fig_4

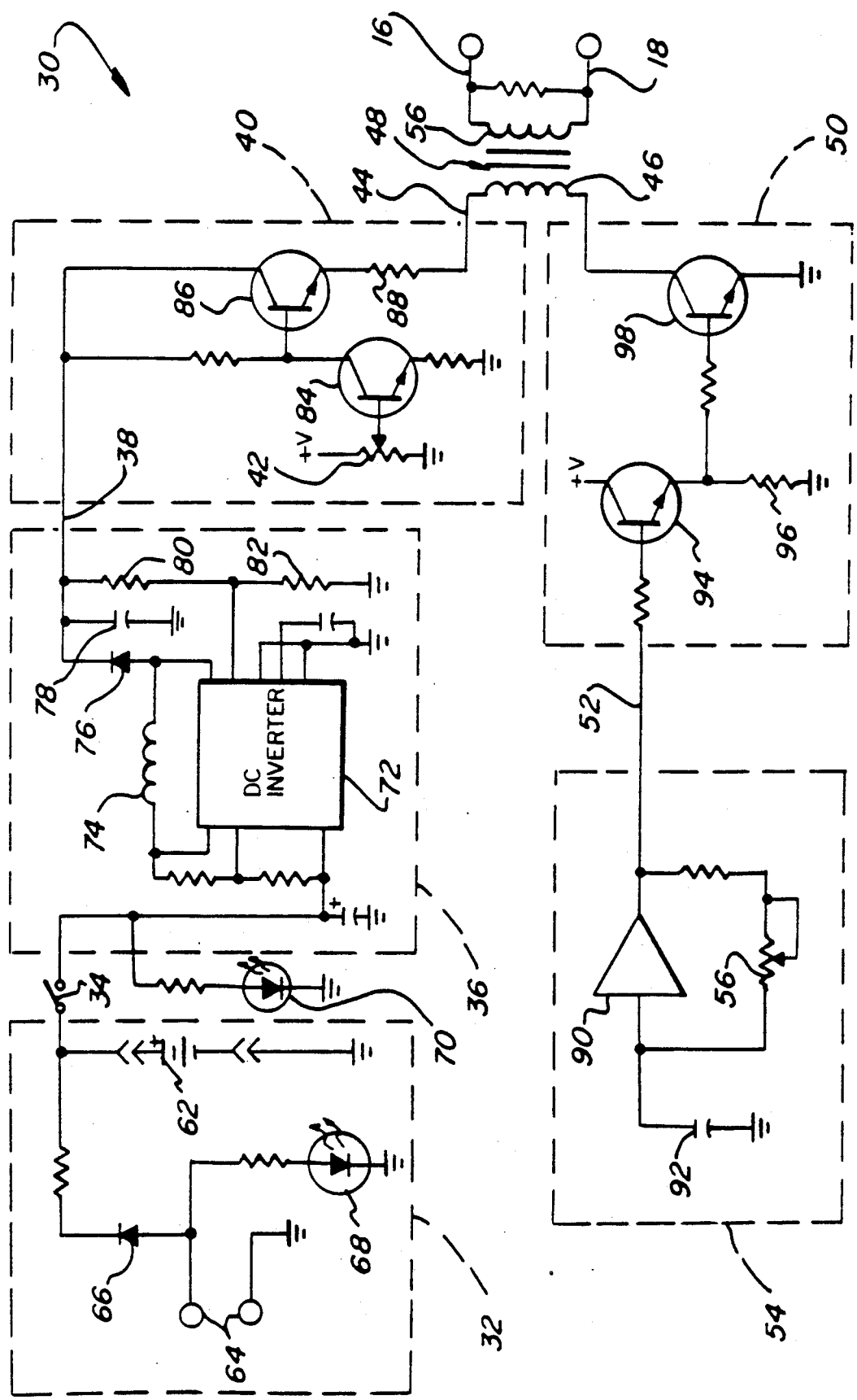
Fig_5

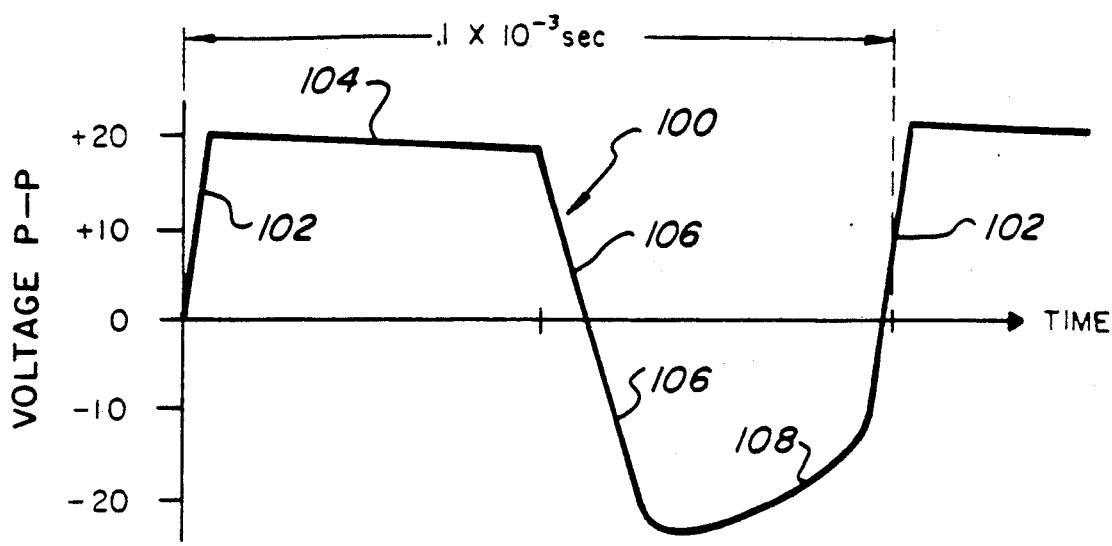
Fig_6A
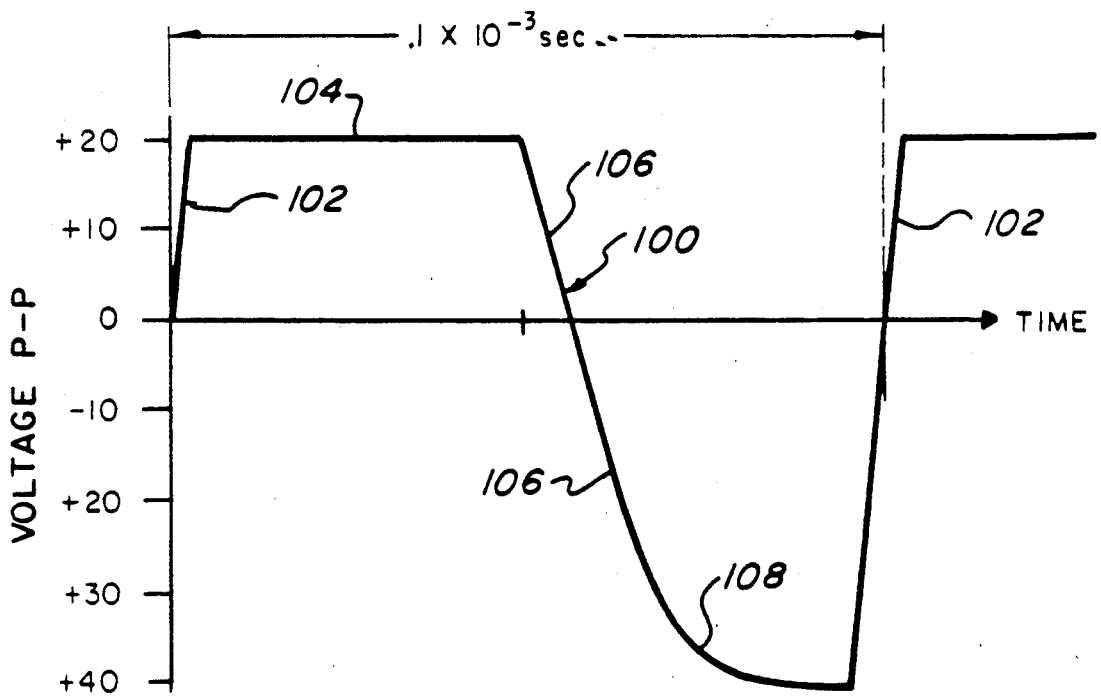
Fig_6B

HIGH FREQUENCY HIGH INTENSITY TRANSCUTANEOUS ELECTRICAL NERVE STIMULATOR AND METHOD OF TREATMENT

BACKGROUND OF THE INVENTION

1. Field of the Invention

This invention relates to transcutaneous electrical nerve stimulation and more particularly to a new and improved apparatus and process of applying relatively high frequency and high intensity pulses of electrical energy to the skin of a patient in order to obtain improved medical results such as blocking pain for a traumatic or medical procedure.

2. Description of the Prior Art

Transcutaneous electrical nerve stimulation (TENS) is a well known medical treatment used for symptomatic relief and management of chronic intractable pain, and as an adjunctive treatment in the management of post surgical and post traumatic acute pain. TENS involves the application of electrical pulses to the skin of a patient. Electrodes are located at selected locations on the patient's skin and the electrical energy is transferred between the two electrodes. The electrical energy is usually applied in the form of mild, electrical impulses. The impulses pass through the skin and interact with the nerves that lie underneath the skin. The electrical impulses act on the nervous system in such a way as to suppress the sensation of pain that would otherwise serve as a protective mechanism. As a symptomatic treatment, TENS has proven to effectively reduce pain for patients suffering from chronic or acute pain. TENS has no capacity for curing the cause of the pain, but simply interacts with the nervous system to suppress or relieve the pain.

The typical TENS system includes the TENS stimulator, lead wires and electrodes which are connected to the skin of the patient. The TENS stimulator is, in effect, an electrical pulse generator which delivers the electrical pulses or impulses at a predetermined fixed or selectable frequency. Typical prior TENS frequency treatment ranges have been in terms of hundreds of pulses per second. In many cases, the treatment frequency is fixed by the design of the electrical pulse generator, or is established as a preselected, generally arbitrary rate at the time of treatment. Most typical TENS pulse generators allow adjustment of the intensity or amplitude of the pulses delivered. The typical intensity ranges in the neighborhood of less than 100 volts peak to peak. The electrical impulses applied have taken a variety of different forms. For example, symmetrical sinusoidal wave forms, symmetrical biphasic wave forms and DC needle spikes have all been applied in various TENS treatments. Each of the wave forms are believed to offer some advantage, although there has been no clear previous consensus that any particular type of wave form is more advantageous than another type.

Furthermore, the prior TENS has typically been used for pain reduction rather than as an analgesic or pain-blocker in order to allow the performance of a traumatic or medical procedure upon a patient and there has been a long felt need for an analgesic or pain-blocker for certain medical procedures. For example, the use of electrolysis to remove hair from a patient's upper lip typically is painful to a patient and causes swelling. It is typical for a patient to only be able to tolerate from a few seconds to several minutes of electrolysis. Similarly, pain, discomfort and anxiety are common in electrolysis for hair removal in many anatomical sites in the human body.

It is against this background information, and other information, that the present invention has resulted.

SUMMARY OF THE INVENTION

A number of significant improvements and advancements in the field of electrolysis and surgery are available as a result of the present invention. Many traumatic or medical procedures which would typically produce pain and swelling in the skin of a patient can be performed with the use of the TENS device of the present invention. These significantly improved medical results are obtained by applying the TENS electrical impulses at substantially higher frequencies than have previously been used or recognized. In addition, the high frequency of the TENS impulses is adjusted or selected for optimal medical results. Further, each electrical impulse is preferably of a predetermined wave form characteristic which is believed to substantially increase and enhance the TENS effect and reduce swelling. Many other improvements will be apparent and discovered upon full comprehension and application of the aspects of this invention.

In accordance with one of its aspects, the present invention pertains to a method of TENS stimulation in which a relatively high frequency, preferably in the neighborhood of between 2.5 kilohertz and 60 kilohertz, is applied to the patient. For reasons not fully understood at the present time, the relatively higher frequency seems to stimulate an increased TENS effect with reduced swelling.

In accordance with another of its aspects, the present invention allows the relatively high frequency of impulses to be selected to optimize the relief obtained by the patient. The method involved is to initially apply the impulses at the high end of the high frequency range and at the low end of the amplitude or intensity range. The amplitude of the electrical impulses is adjusted to a level for the particular TENS treatment session, preferably at a mid-level. The frequency is then selectively decreased in order to maximize the stimulation effect until the patient senses a motor nerve response or "tingling". By adjusting both the intensity and the frequency in this manner, the treatment is optimized for each patient.

According to a further aspect of the present invention, the electrical impulse to the patient is preferably an AC wave form which includes a square wave portion forming the first positive half cycle of the AC wave form followed by a generally negative rounded pulse portion forming the negative half cycle of the AC wave form. The square wave portion is characterized by a relatively fast rise time, a sustained or slightly decreasing amplitude level over the majority of the time of the square wave portion and a slower fall time. The fall time slope generally characterizes the initial significant portion of the negative rounded pulse portion. The negative portion thereafter returns to the baseline to commence another AC wave form repetition. The energy within the positive going square wave and the negative rounded wave is generally equal, thereby transferring a zero net DC charge to the patient.

A more complete understanding and appreciation of the present invention can be obtained by reference to the accompanying drawings, which are briefly described below and from the detailed description of a presently preferred embodiment, and from the appended claims.

BRIEF DESCRIPTION OF THE DRAWINGS

FIG. 1 is a generalized illustration of the method of treating a patient with TENS, using a TENS stimulator connected to at least one pair of electrodes attached to the skin of the patient.

FIG. 2 is a block diagram of one embodiment of the TENS stimulator which may be used as shown in FIG. 1.

FIG. 3 is a block diagram of an output portion of the TENS stimulator shown in FIG. 2, illustrating an alternative embodiment providing two output channels driven by a single power driver.

FIG. 4 is a block diagram of another embodiment of the TENS stimulator, providing two separate output channels, each of which is driven by its own power driver.

FIG. 5 is a schematic circuit diagram of the stimulator in FIG. 2, which is duplicated for each output channel of the TENS stimulator shown in FIG. 4.

FIGS. 6A and 6B are diagrams of a single pulse of a repetitive AC output wave form supplied by the TENS stimulator shown in FIGS. 2 and 4.

DETAILED DESCRIPTION

The treatment of a human patient 10 with a TENS unit in accordance with the present invention is illustrated in FIG. 1. Lacerations 11 requiring sutures are shown on the patient 10. A pair of conventional electrodes 12 and 14 are attached to the patient's skin in a predetermined location adjacent one of the lacerations 11 to alleviate or block pain so that sutures may be applied with little or no pain to close the laceration. The electrodes 12 and 14 are respectively connected by conductors 16 and 18 to a TENS stimulator 20. Pulses of electrical energy are delivered through the conductors 16 and 18 to the electrodes 1 and 14, where they are conducted into the skin to stimulate the nerves and achieve a TENS medical effect.

Preferably the TENS stimulator of the present invention provides two output channels for stimulating two separate areas of the patient 10. For example, the TENS stimulator 20 has one output channel to which the electrodes 12 and 14 and the conductors 16 and 18 are connected. A second output channel connects electrodes 22 and 24 by conductors 26 and 28, respectively, to the TENS stimulator. It has been determined that in some acute pain situations, the application of two separate TENS impulses between two pairs of electrodes is very effective in stimulating favorable patient treatment.

A single channel TENS stimulator 30 is illustrated in FIG. 2. The stimulator 30 includes a power supply 32 which preferably takes the form of a rechargeable battery. The battery is connected by a switch 34 to a DC inverter 36. The DC inverter converts the relatively lower DC voltage level of the battery power supply 32 to a relatively higher DC level and applies that higher DC level at 38 to a voltage control 40. A potentiometer 42 controls the voltage control 40 to adjust the output voltage at 44 between ground reference and the maximum voltage at 38 The voltage at 44 is applied to a primary winding 46 of an output transformer 48. Current is conducted through the primary winding 46 by a power driver 50 connected to the other terminal of the primary winding 46. Signals 52 from an oscillator 54 control the power driver 50. Preferably the signals are square wave signals supplied by the oscillator 54, and the power driver 50 responds to the square wave signals by conducting current through the primary winding 46 in relation to the on times of the square wave signal 52. A potentiometer 56 adjusts the frequency of the oscillator 54.

Output signals are derived by the secondary winding 58 of the transformer 48. The output signals are supplied on the electrodes 16 and 18, for example, to the patient electrodes 12 and 14 (FIG. 1). Use of the output transformer 48 effectively supplies the output pulses centered relative to ground level, and thereby transfers a zero net DC charge to the patient.

Use of the voltage control 40 to control the level of DC voltage at 44, by use of the potentiometer 42, establishes the intensity or amplitude of the output signal applied from the secondary winding 58 of the transformer 48. The power driver 50, as will be explained in greater detail below, essentially conducts the amount of current established by the potential at 44 through the primary winding. The potentiometer 56 controls the frequency of the oscillator 54 to thereby control the frequency of pulses delivered from the output transformer 48. Of course, in place of the potentiometers 42 (intensity) and 56 (frequency) any other suitable means for control may be substituted, such as digitally controlled potentiometers working in conjunction with a microprocessor. A microprocessor might further be utilized in the present invention to drive displays of the frequency and intensity information.

The relative size of the battery of the present invention is significantly larger than most batteries of TENS devices which are adapted to be worn by the patient Due to the relatively high electrical power requirements which have been determined to be desirable for TENS treatment, the power supply 32 should be a relatively large battery capable of being recharged. Considerable electrical power is consumed by the relatively high energy pulses created by the voltage level at 44 and switched through the primary winding 46 by the power driver 50.

In another embodiment of the TENS stimulator, a single output transformer 48 and power driver 50 are used in a TENS stimulator to obtain two output channels, as is shown in FIG. 3. The remainder of the circuit not shown in FIG. 3 is the same as that described in conjunction with FIG. 2. As can be appreciated, two conductors 16 and 26 are connected to one end of the secondary winding 58 and another pair of conductors 18 and 28 are connected to the other end of the secondary winding 58 of the output transformer 48. The single output signal developed across the output winding 58 is thus applied to each separate pair of conductors 16, 18 and 26, 28. While the arrangement shown in FIG. 3 has the advantage of cost reduction, it does reduce the magnitude of the signals applied on the conductor pairs 16, 18 and 26, 28 by an equal amount, since the conductor pairs are connected in parallel to separate parallel impedances through the patient Thus, equal intensities or voltages of output signals are applied on both of the conductor pairs 16, 18 and 26, 28.

A third embodiment 60 of the TENS stimulator, which allows true independent control over the output signal pulses delivered over two separate output channels, is illustrated in FIG. 4. A single power supply and DC inverter 36 are used, and the remainder of the components are essentially duplications of those described in conjunction with the TENS stimulator 30 shown in FIG. 2. As such, the duplicated components for one channel are labeled with reference numerals ending in a subscript a, and those duplicated components used in the second channel are labeled with reference numbers ending in a subscript b. In all regards, each of the channels in the TENS stimulator 60 operate similarly and in the manner previously described in conjunction with the TENS stimulator 30 shown in FIG. 2.

It should be noted that the magnitude of the output signal pulses from secondary windings 58a and 58b of transformers 48a and 48b are separately and independently adjustable by the potentiometers 42a and 42b, respectively. Similarly, the frequency of application of the output pulses from the two channels are separately and independently adjustable by the potentiometers 56a and 56b. Thus, the output signal pulses supplied by each channel are separately controllable and adjustable in frequency and amplitude for each channel.

The TENS stimulator 30, and the essential portions duplicated to obtain the TENS stimulator 60 shown in FIG. 4, are shown in greater detail in schematic form in FIG. 5.

The power supply 32 includes a conventional rechargeable battery 62. In addition, charging jacks 64 are connected by diode 66 across the battery 62. The charging jacks 64 will be utilized either to power the TENS stimulator 30 from a conventional DC power supply which may be driven by AC power, or to charge the rechargeable battery 62. An LED 68 is also provided to indicate the application of power at the charging jacks 64. Power from the power supply 32 is connected by the switch 34 to the DC inverter 36. Another LED 70 is provided to signal the operation of the TENS device when the switch 34 is closed A variety of different circuits for the power supply can be employed.

The DC inverter 36 utilizes a conventional DC inverter integrated circuit (IC) 72. The IC 72 is connected in the conventional manner illustrated. An inductor 74 is connected between two terminals of the IC 72, and switching currents therethrough develop relatively high voltage spikes. The resulting high voltage spikes are rectified by a diode 76. The rectified spikes charge a relatively high capacity filter capacitor 78. The maximum DC voltage level signal 38 is available between the terminals of the filter capacitor 78. Feedback resistors 80 and 82 supply a feedback signal to the IC 72 for the purpose of regulating the output voltage to the fixed maximum level. Preferably the ICU 72 is a commercial part, Motorola No. MC34063P1. Preferably the inductor 74 is a 200 microhenry, 1.5 amp component. A variety of different circuits for the inverter 36 can be employed.

The voltage control 40 receives the maximum DC output signal 38. The voltage control 40 includes a biasing transistor 84 and a regulating transistor 86. The base of the biasing transistor 84 is connected to the potentiometer 2. The voltage level from the potentiometer 42 establishes the conductivity of the biasing transistor 84. The level of conductivity of the biasing transistor 84 establishes the signal applied to the base of the regulating transistor 86, thereby causing transistor 86 to regulate the output voltage at 44 to a predetermined level established by the potentiometer 42. A resistor 88 in series with the emitter of the regulating transistor 86 further limits the amount of current drawn from the filter capacitor 78 through the primary winding 46 of the output transformer 48. A number of alternative circuits for the voltage control can be employed.

The oscillator 54 is of a conventional configuration which utilizes an operational amplifier 90 in conjunction with a feedback network which includes the potentiometer 56 and a capacitor 92 connected to its input terminal. The output signal 52 from the oscillator 54 is substantially a square wave having a frequency established by the resistance of the potentiometer 56 in the feedback network connected to the input terminal of the operational amplifier 90. A variety of other conventional square wave oscillator circuits can be employed The square wave signal 52 is applied to the power driver 50. The power driver 50 includes a first switching transistor 94 which receives the square wave signal 52 at its base terminal. When the square wave signal 52 is high, the switching transistor 94 is conductive and a positive signal is developed across resistor 96. The positive signal across resistor 96 is applied to the base terminal of a power switching transistor 98 to render it conductive. When conductive, the power switching transistor 98 conducts current through the primary winding 46 of the output transformer 48. When the square wave signal at 54 is low, the transistors 94 and 98 are non-conductive. A number of different types of power driver circuits 50 could be employed, but, as will be described below, the power driver circuit 50 should preferably retain the capability to achieve the desirable characteristics of the output wave form.

The amount of energy conducted through the primary winding 46 is determined in large measure by the voltage level at 44, which is developed by the regulating transistor 86, and by the magnitude of the current conducted through the primary winding as controlled by the regulating transistor 86. Thus, the voltage control essentially controls the intensity of the treatment the patient receives, while the power driver actually develops the signals applied to the patient by switching signals through the primary winding 46 of the transformer 48. The signal in the primary winding 46 establishes the maximum intensity or amplitude of the output signal induced in the secondary winding 56 of the output transformer 48. Of course, increasing the frequency of the square wave pulses 52 from the oscillator 54 thereby controls the frequency of the electrical impulses delivered from the TENS stimulator 30. Changing the frequency of the output pulses does not significantly change the magnitude of the energy delivered to the patient.

FIGS. 6A and 6B illustrate the signal characteristics of an output pulse wave form 100 provided at the secondary winding 56 of the output transformer 48. FIG. 6A exemplifies the output pulse wave form delivered into a 500 ohm resistive load, while FIG. 6B exemplifies the output wave form delivered to a 10,000 ohm resistive load.

The wave form 100 shown in FIG. 6A is centered about a zero reference potential or base line. Centering the wave form 100 is attained by the inherent functionality of the output transformer 48. As a result of this centering, the amount of charge transferred during a first half cycle, represented by that square wave portion above the zero reference, and the amount of charge transferred during a second half cycle portion, represented by the negative rounded pulse portion below the reference line, are equal. Therefore, a zero net charge transfer to the patient occurs.

As will be noted by comparing FIG. 6A and 6B, the first positive square wave portion of each wave form is essentially the same. This positive portion is characterized generally as a square wave having a relatively rapid rise time, or leading edge, shown at 102, a relatively constant or slightly decreasing maximum value at 104 which is sustained during the majority of the time that the positive portion occurs, and by a relatively slower fall time, or trailing edge, shown at 106. The amount of decrease at 104 depends substantially on the resistive component of the load between the electrodes (FIG. 1) attached to the patient's body, with greater resistances achieving lesser reductions or decreases.

The slope of the trailing edge 106 continues into the negative portion and may continue to curve in various configurations shown at 108 when another output pulse 100 is generated by the TENS stimulator 30. The ending curve of the negative portion is characterized by a relatively rapid rise time of the same slope as the leading edge 102 of the positive square wave portion.

The relatively rapid rise time and relatively slower fall time of the output wave form are achieved as a result of the inherent collector to base capacitance in the power switching transistor 98, shown in FIG. 5. This capacitance allows the collector voltage of the power switching transistor 98 to rapidly change, thereby inducing a high charging current in the primary winding. However, after this inherent base to collector capacitance has been charged during the time that the power switching transistor 98 is conductive, the current flow through the secondary winding is relatively more slowly terminated when the power switching transistor 98 becomes nonconductive. Thus, the relatively slower fall time (106, FIGS. 6A and 6B) is created in the output pulse. During the mid-region 104 of the square wave portion, the current flow through the primary winding increases at a relatively uniform rate to obtain the sustained output voltage at 104.

For reasons which are not readily understood at the present time, a square wave portion having the relatively rapid rise time and the relatively slower fall time seems to provide an additional beneficial effect in patient treatment using TENS. It appears as though the significant aspects of the square wave which give rise to this improvement are the relatively rapid rise time and the relatively slower fall time.

To utilize the TENS stimulator of the present invention on a patient, the electrodes are attached to the patient and the conductors connect the output terminals of the output transformer 48 to the electrodes. Prior to turning the power on, the frequency potentiometer 56 is manually preset to provide the maximum output pulse delivery frequency upon energization, which is preferably about 60 kilohertz. The intensity potentiometer 42 is also manually preset to provide a relatively low amplitude or intensity for the output signal pulse upon energization. The switch 34 is then closed to energize the circuit and the intensity potentiometer 42 is adjusted to increase the amplitude or intensity of the output signal pulses to a mid-level, or until the patient begins to receive a sensation or tingling. Thereafter the frequency is adjusted downwardly with the frequency potentiometer 56 from its maximum level until the patient begins to sense a stimulation caused by a lower frequency of application of electrical impulses. Generally speaking the frequency at which the patient begins to sense the application of electrical impulses is an optimum one for that particular patient, and it will generally fall within the range of 2.5 kilohertz to 60 kilohertz. The amount of the stimulation should not be such as to induce pain, but should be a relatively comfortable sensation.

At this time, the medical procedure, such as applying sutures or performing electrolysis, may be performed. With time, the patient may need to adjust the frequency downwardly from the previous level to maintain the tingling sensation whereby there is an increase in the level of analgesia produced. These rises in analgesia continue throughout treatment in response to slight decreases in frequency. This constant adjustment in frequency may be carried out by the patient, by means of a hand-held remote control device (not shown) that includes a button for easily decreasing the frequency as the clinical sensation of tingling decreases. This control of pain reduction by the patient is one of the theories proposed for the efficacy of the present invention, since it removes the feeling of "lack of control" in an environment associated with pain, discomfort and anxiety.

By providing the independent adjustment of frequency, relatively high frequency application of TENS to a patient is possible. Furthermore, by adjusting the frequency of the TENS application separately and particularly for each patient, the optimum TENS treatment frequency for the patient may be obtained. However, the frequency level is slowly and gradually adjusted throughout the whole treatment session resulting in increased analgesia. The application of the output pulse wave form having a square wave positive portion with a relatively rapid rise time leading edge and relatively longer fall time trailing edge, increases the effective stimulation and treatment of the patient.

It is believed that the present invention obtains the desired results due to the fact that the electrical impulses generated thereby influence the nerve cells to produce natural substances such as Beta-endorphins, GABA, norepinephrine, dopamine, enkephalin, substance P and somatostatin, which produce analgesia and inhibitory action on nociceptive dorsal horn neurons and trigger reactions such as the secretion of serotonin, a naturally occurring neurotransmitter which controls and raises the pain threshold level. In addition, the electrical impulses may act to block the natural nerve pain impulses travelling along A delta and C delta nociceptive fine afferent nerve fibers. Thus, the treatment of the present invention appears to be effective as a result of the combination of blocking the pain impulses, triggering the reaction of various naturally occurring body elements to increase analgesia as well as raising the pain threshold and inhibiting cells in important pain pathways in the spinal cord to the brian. Although these are theories based on actual observations, the present invention has proved effective in relief of chronic and acute pain far in excess of prior TENS devices.

In an experimental treatment with the present invention used in conjunction with electrolysis to remove facial hair on forty-two patients, the following results were shown, as evaluated by the patients themselves after orientation sessions describing how to relay pain reduction during treatment. The patients had pain reduction during treatment that ranged from fifty to one hundred percent. Of the forty-two patients treated, only one had any signs of slight swelling as a result of treatment which normally would have resulted in swelling for all forty-two patients. Furthermore, among patients too sensitive to tolerate more than a few minutes of electrolysis without the present invention, it was possible to use the TENS stimulator of the present invention for up to one hour of electrolysis without pain, discomfort and anxiety, yet with a feeling of complete relaxation for the patient. This lack of pain, anxiety and adverse skin reaction continues for several hours after the patient leaves the professional's office. Therefore, there is no post operative pain, discomfort or swelling.

Presently preferred embodiments of the invention have been described above with a degree of specificity. It should be understood, however, that this description has been made by way of preferred example and that the invention itself is defined by the scope of the appended claims.

The invention claimed is:

1. A method for blocking the pain caused by a traumatic or medical procedure on a patient with the use of transcutaneous electrical nerve stimulation, comprising the steps of:
    (a) generating a series of electrical pulses at a frequency in the range of 2.5 to 60 kilohertz;
    (b) applying said generated electrical pulses to a desired area on a patient's body;
    (c) electrically conducting the applied electrical pulses through the patient's body to stimulate selected nerves; and
    (d) performing the procedure.

2. A method as defined in claim 1 wherein generating the series of electrical pulses includes:
    generating the electrical pulses with an electrically powered stimulator; and
    electrically isolating the patient from the stimulator.

3. A method as defined in claim 2 wherein electrically isolating the patient from the stimulator comprises coupling a signal generated by the stimulator through a transformer to the patient.

4. A method as defined in claim 1 wherein the generating step further comprises adjusting the frequency of the electrical pulses within said range.

5. A method as defined in claim 4 further comprising adjusting the high frequency electrical pulses to 60 kilohertz.

6. A method as defined in claim 4 wherein generating the series of electrical impulses further comprises adjusting the intensity of the electrical pulses.

7. A method as defined in claim 6, further comprising the additional steps of:
    (e) adjusting the frequency to the highest frequency within the frequency adjustment range;
    (f) adjusting the intensity to the lowest intensity within the intensity adjustment range; then
    (g) adjusting the intensity to a level which is slightly below that level which achieves perceptible nerve sensation to the patient;
    (h) adjusting the frequency downward from the highest frequency to a relatively lower frequency until the patient begins to perceive a nerve sensation; and
    (i) continuing to adjust the frequency downwardly as necessary throughout the procedure to maintain the nerve sensation.

8. A method as defined in claim 1 further including forming the high frequency electrical pulses to include a square wave portion and an opposite polarity pulse centered about a zero reference potential.

9. A method as defined in claim 8 further comprising forming the square wave portion with a leading edge having a relatively rapid rise time and with a trailing edge having a relatively slower fall time.

10. An apparatus for blocking the pain caused by a traumatic or medical procedure on a patient with the use of transcutaneous electrical nerve stimulation, comprising:
    source means for supplying a source of relatively high DC voltage;
    voltage control means connected to said source means and receptive of the relatively high DC voltage and operative for supplying a controllable level of the DC voltage;
    an output transformer means having a primary and a secondary winding, the primary winding connected to said voltage control means and receptive of the controlled DC voltage level supplied by said voltage control means, the transformer means operatively inducing in the secondary winding an electrically isolated output signal of approximately the same frequency as the signal in the primary winding and with an amplitude characteristic proportional t the amplitude characteristic of the signal in the primary winding;
    oscillator means operative for generating a square wave oscillator signal;
    power driver means connected to the other end of said primary winding of said output transformer means, the power driver means receptive of said square wave oscillator signal and operative for switching current through the primary winding at a frequency related to the frequency of the oscillator square wave signal;
    the secondary winding of said transformer means supplying an output signal in response to the conduction of the power driver means, the output signal being a wave form which includes a square wave portion of one polarity having a leading edge with a relatively rapid rise time and a trailing edge with a relatively slower fall time and a pulse portion of the opposite polarity; and
    a pair of electrodes connected to the secondary winding of said output transformer means for conducting the output signal to the skin of a patient.

11. Apparatus as defined in claim 10, further comprising:
    adjustment means connected to said oscillator means and operative for adjusting the frequency of the oscillator square wave signal.

12. Apparatus as defined in claim 11, further comprising:
    adjustment means connected to said voltage control means and operative for adjusting the level of the controlled voltage.

13. Apparatus as defined in claim 11 wherein said square wave oscillator signal is adjustable within a range of 2.5 kilohertz to 60 kilohertz.

14. Apparatus as defined in claim 10 wherein the power driver means conducts current through the primary winding during one state of the square wave oscillator signal and does not conduct current through the primary winding during the other state of the square wave oscillator signal, and said square wave signal has a predetermined frequency within the range of 2.5 kilohertz to 60 kilohertz.

15. Apparatus as defined in claim 14 further comprising:
    a second pair of electrodes connected in parallel with said first electrodes.

16. Apparatus as defined in claim 14 further comprising:

a first output channel comprising the source means, the voltage control means, the output transformer means, the oscillator means, the power driver means, and the pair of electrodes, all as first aforesaid; and a second output channel comprising the first said source means, a second said voltage control means, a second said output transformer means, a second said oscillator means, a second said power driver means, and a second pair of electrodes.

17. A method for blocking the pain caused by a traumatic or medical procedure on a patient with the use of transcutaneous electrical nerve stimulation, comprising the steps of:

(a) generating a high frequency series of electrical pulses;

(b) adjusting the frequency of the pulses to a relatively high rate;

(c) adjusting the intensity of the pulses to a relatively low level;

(d) applying said generated pulses to a desired area on a patient's body;

(e) adjusting the intensity of the pulses to a desired level;

(f) adjusting the frequency of the pulses to a relatively lower frequency until the patient begins to perceive a nerve sensation; and (g) continuing to adjust the frequency downwardly as necessary throughout the procedure to maintain the nerve sensation.

18. A method as defined in claim 17 wherein the high frequency electrical pulses can be adjusted within the frequency range of 2.5 to 60 kilohertz.

19. A method as defined in claim 17 further including forming the high frequency electrical pulses to include a square wave portion and an opposite polarity pulse centered about a zero reference potential.

20. A method as defined in claim 19 further comprising forming the square wave portion with a leading edge having a relatively rapid rise time and with a trailing edge having a relatively slower fall time.

* * * * *

UNITED STATES PATENT AND TRADEMARK OFFICE
CERTIFICATE OF CORRECTION

PATENT NO. : 5,052,391

DATED : 10/01/91

INVENTOR(S) : Silverstone et al

It is certified that error appears in the above-identified patent and that said Letters Patent is hereby corrected as shown below:

Title Page:

Item [19] "Silberstone et al" should read --Silverstone et al--.

Item [75] "Leon M. Silberstone" should read --Leon M. Silverstone--.

Signed and Sealed this

Second Day of March, 1993

Attest:

STEPHEN G. KUNIN

*Attesting Officer*     *Acting Commissioner of Patents and Trademarks*